(12) United States Patent
DeCaire et al.

(10) Patent No.: US 8,071,079 B2
(45) Date of Patent: *Dec. 6, 2011

(54) PERSONAL CARE APPLICATIONS OF EMULSIONS CONTAINING ELASTOMERIC SILANES AND SILOXANES WITH NITROGEN ATOMS

(75) Inventors: Julie Sue DeCaire, Auburn, MI (US); Bethany Johnson, Midland, MI (US); Michael Richard Lafore, Freeland, MI (US); Zuchen Lin, Midland, MI (US)

(73) Assignee: Dow Corning Corporation, Midland, MI (US)

( * ) Notice: Subject to any disclaimer, the term of this patent is extended or adjusted under 35 U.S.C. 154(b) by 1545 days.

This patent is subject to a terminal disclaimer.

(21) Appl. No.: 10/552,537

(22) PCT Filed: Apr. 15, 2004

(86) PCT No.: PCT/US2004/011535
§ 371 (c)(1),
(2), (4) Date: Jul. 10, 2006

(87) PCT Pub. No.: WO2004/103326
PCT Pub. Date: Dec. 2, 2004

(65) Prior Publication Data
US 2006/0269506 A1    Nov. 30, 2006

Related U.S. Application Data

(60) Provisional application No. 60/471,059, filed on May 16, 2003.

(51) Int. Cl.
*A61Q 5/02* (2006.01)
*A61Q 5/04* (2006.01)
*A61Q 5/06* (2006.01)
*A61Q 5/08* (2006.01)
*A61Q 5/10* (2006.01)
*A61Q 5/12* (2006.01)
*A61Q 1/08* (2006.01)
*A61Q 1/06* (2006.01)
*A61Q 1/12* (2006.01)

(52) U.S. Cl. ............... 424/70.12; 424/70.2; 424/70.6; 424/70.7; 424/47; 424/63; 424/64; 424/65; 424/69; 424/401; 424/402

(58) Field of Classification Search ............... None
See application file for complete search history.

(56) References Cited

U.S. PATENT DOCUMENTS

| | | |
|---|---|---|
| 4,902,499 A | 2/1990 | Bolish, Jr. et al. |
| 5,389,364 A | 2/1995 | Cifuentes et al. |
| 5,409,695 A | 4/1995 | Abrutyn et al. |
| 5,419,627 A | 5/1995 | Oldinski |
| 5,504,149 A | 4/1996 | Kosal |
| 6,482,969 B1 | 11/2002 | Helmrick et al. |
| 6,607,717 B1 | 8/2003 | Johnson et al. |
| 6,787,603 B2 * | 9/2004 | Johnson et al. ......... 524/838 |
| 6,803,399 B2 | 10/2004 | Ferritto et al. |
| 2006/0193805 A1 * | 8/2006 | Johnson et al. ......... 424/70.12 |

* cited by examiner

*Primary Examiner* — Jyothsna Venkat
(74) *Attorney, Agent, or Firm* — Alan Zombeck

(57) ABSTRACT

Oil-in-water (O/W) and water-in-oil (W/O) emulsions and microemulsions containing elastomeric silanes or siloxanes preferably having quaternary ammonium groups are generally made by reacting organic quaternary ammonium compounds having epoxide groups or halohydrin groups, with silanes or siloxanes having amino groups. The reaction is carried out in an aqueous polar phase containing a crosslinking agent and surfactant. The emulsions and microemulsions are especially useful for treating hair, skin, or the underarm.

9 Claims, No Drawings

PERSONAL CARE APPLICATIONS OF EMULSIONS CONTAINING ELASTOMERIC SILANES AND SILOXANES WITH NITROGEN ATOMS

CROSS REFERENCE TO RELATED APPLICATIONS

This application is a U.S. national stage filing under 35 U.S.C. §371 of PCT Application No. PCT/US2004/011535 filed on Apr. 15, 2004, currently pending, which claims the benefit of U.S. Provisional Patent Application No. 60/471,059 filed May 16, 2003 under 35 U.S.C. §119 (e). PCT Application No. PCT/US2004/011535 and U.S. Provisional Patent Application No. 60/471,059 are hereby incorporated by reference.

This invention is directed to the use in personal care applications of certain oil-in-water (O/W) emulsions and microemulsions and water-in-oil (W/O) emulsions and microemulsions containing elastomeric silanes or siloxanes having nitrogen atoms, preferably quaternary ammonium groups as an oil phase. In particular, the preferred elastomeric silanes or siloxanes are obtained by reacting organic quaternary ammonium compounds having epoxide or halohydrin groups, with silanes or siloxanes having amino groups; and the reaction is carried out in the presence of a crosslinking agent and a surfactant in an aqueous polar phase.

Copending application U.S. Ser. No. 10/306,012, filed Nov. 27, 2002, entitled Method of Making Emulsions Containing Quaternary Ammonium Functional Silanes and Siloxanes (the '012 application); copending application U.S. Ser. No. 10/001,760, filed Oct. 24, 2001, entitled Silicon Based Quaternary Ammonium Functional Compositions and Methods for Making Them, now U.S. Pat. No. 6,482,969, issued Nov. 19, 2002, (the '969 patent); and copending application U.S. Ser. No. 10/001,753, filed Oct. 24, 2001, entitled Silicon Based Quaternary Ammonium Functional Compositions and Their Applications (the '753 application), are all assigned to the same assignee as the present application, and incorporated herein by reference.

As noted in the '012 application, the '969 patent, and the '753 application, quaternary ammonium functional silanes and quaternary ammonium functional siloxanes have a variety of commercial application in the textile industry and in the personal care arena They can also be used as anti-microbial agents; in modifying fillers, fibers, and surfaces; as thickening agents; and as a conditioning agent.

In many of these applications and uses, it is often necessary to deliver the quaternary ammonium functional silanes and the quaternary ammonium functional siloxanes as an emulsion or microemulsion. When an emulsion is required, conventional wisdom dictates that the quaternary ammonium functional silane or quaternary ammonium functional siloxane be combined with a surface active agent and water, and mixed until the emulsion is formed.

It is often inconvenient for end users of quaternary ammonium functional silanes and siloxanes to prepare emulsions and microemulsions, and so it would be beneficial to provide a new and simpler process for preparing the emulsions.

While the '753 application describes a method of making emulsions containing quaternary ammonium functional silanes and quaternary ammonium functional siloxanes, the process involves application of conventional wisdom, i.e., the quaternary ammonium functional silane or siloxane is combined with a surface active agent and water, and mixed until an emulsion is formed.

The process of making the emulsions and microemulsions according to the present application however, differs significantly from the process used in the '753 application, in that quaternary ammonium functional silanes or siloxanes are actually synthesized in an emulsion, using monomers as starting materials which are reacted together to form the quaternary ammonium functional silane or siloxane, rather than using quaternary ammonium functional silanes or siloxanes. In addition, the quaternary ammonium functional silanes or siloxanes present in the emulsions according to the present invention are elastomers in contrast to fluids which are formed in the emulsion of the '753 application.

In today's hair care market, there continues to exist unmet needs for flexible styling benefits in hair care compositions. For example, when using organic resins to style hair, the hair tends to become rigid or brittle. In addition, organic resins do not typically provide conditioning properties to hair. This invention, however, demonstrates that flexible styling benefits can be obtained, as well the provision of conditioning properties to hair.

This invention relates to the use in personal care, especially hair care, of certain oil-in-water (G/W) or water-in-oil (W/O) emulsions and microemulsions containing organosilicon compositions as the oil phase. In particular, these emulsions and microemulsions contain elastomeric silanes or siloxanes preferably having quaternary ammonium groups in their molecule as the oil phase, the elastomeric silanes or siloxanes having quaternary ammonium groups having been obtained by reacting (i) an organic quaternary ammonium compound having epoxide groups or halohydrin groups in its molecule, with (ii) a silane or siloxane having amino groups in its molecule, in the presence of (iii) a crosslinking agent, (iv) a surfactant, dispersed in (v) an aqueous polar phase.

Representative of suitable quaternary ammonium compounds having epoxide groups and halohydrin groups are glycidyl trimethylammonium chloride, and (3-chloro-2-hydroxypropyl)trimethylammonium chloride, respectively. The aqueous polar phase may be water, or a mixture of water and a polar organic compound, such as 1,2-hexanediol. These emulsions and microemulsions are useful especially as treating agents for the hair, as well as for application to the skin and underarm areas of the human body.

In particular, the emulsions demonstrated curl retention properties determined by standard test protocols, when the emulsions were tested as dilute leave-on applications, as well as a component of aqueous mousse formulations. Hair tresses were observed to have a bounce back characteristic after the tresses were extended to their full length. It was demonstrated that the emulsions containing the elastomeric silanes or siloxanes resulted in a significant reduction in both wet and dry combing forces in rinse-off conditioner formulations. The hair tresses also had a nice smooth feel in both the wet and the dry state. A decrease in combing forces was also observed when the emulsions were added as a components in a shampoo formulation.

These and other features of the invention will become apparent from a consideration of the detailed description.

DESCRIPTION

The oil-in-water (O/W) and water-in-oil (W/O) emulsions and microemulsions contain elastomeric silanes or siloxanes, as noted above, preferably having quaternary ammonium groups in their molecule as the oil phase. The elastomeric silanes or siloxanes having quaternary ammonium groups are obtained by reacting (i) an organic quaternary ammonium compound having epoxide groups or halohydrin groups in its molecule, with (ii) a silane or siloxane having amino groups in its molecule. The reaction of components (i) and (ii) is carried out in the presence of (iii) a crosslinking agent, (iv) a surfactant, dispersed in (v) an aqueous polar phase. According to another less preferred process, as illustrated by Example 2, nitrogen containing elastomers can be obtained using only components (ii) to (v), and omitting component (i).

The Silanes & Siloxanes Containing Quaternary Ammonium Groups

These materials are essentially the reaction product obtained by combining components (i) and (ii). A detailed showing of their composition in terms of its structure can be found in detail in the '753 and '760 applications.

Generally, these materials can be described, for purposes herein, as being silanes or siloxanes having in their molecule at least one unit containing a group such as —R—Z-Q bonded to silicon in which:
R is a divalent hydrocarbon group such as ethylene;
Z is a group such as —N(Q1)—; and
Q is a group such as —CH(R)CH(OH)YN$^+$(R$^1$)(R$^2$)(R$^3$)X$^-$;
wherein:
Q1 is a monovalent hydrocarbon group such as methyl;
Y is a divalent hydrocarbon group such as ethylene;
X is a counter ion such as chloride Cl$^-$;
and R$^1$-R$^3$ are monovalent hydrocarbon groups such as methyl.

A representative example therefore of at least one particularly preferred —R—Z—Q group is CH$_2$CH(OH)CH$_2$N+(CH$_3$)$_2$(CH$_3$)Cl$^-$.

The Organic Quaternary Ammonium Compound with Epoxide Groups

Reference may be had to the '753 and '760 applications for a detailed showing of the generic formulas of compounds of this type. Suffice to say, for the purposes herein, some specific examples of useful compounds of this type are glycidyl trimethylammonium chloride and glycidyl trimethylammonium bromide. While non-terminal epoxides may also be used, terminal epoxides such as the compounds described are generally preferred. Combinations of epoxides may also be employed, as well as combinations of epoxides and the halohydrins noted below.

The Organic Quaternary Ammonium Compound with Halohydrin Groups

Again, reference may be had to the '753 and '760 applications for a detailed showing of the generic formulas of compounds of this type. Suffice to say, for the purposes herein, some specific examples of useful compounds of this type are
(3-chloro-2-hydroxypropyl)trimethylammonium chloride ClCH$_2$CH(OH)CH$_2$N(CH$_3$)$_3$Cl,
(3-chloro-2-hydroxypropyl)dimethyldodecylammonium chloride,
(3-chloro-2-hydroxypropyl)dimethyloctadecylammonium chloride,
(3-chloro-2-hydroxypropyl)trimethylammonium bromide,
(3-chloro-2-hydroxypropyl)dimethyldodecylammonium bromide, and
(3-chloro-2-hydroxypropyl)dimethyloctadecylammonium bromide.

While non-terminal halohydrins may also be used, terminal halohydrins such as the compounds described are generally preferred. Combinations of halohydrins may also be employed, as well as combinations of halohydrins and the epoxides noted above.

The Silanes & Siloxane with Amino Groups

Silanes containing amino groups for use herein generally comprise organosilicon monomers of the type R$_3$SiR wherein the R groups in the molecule can consist of alkyl groups containing 1-6 carbon atoms, such as methyl, ethyl, propyl, isopropyl, butyl, and isobutyl; an aryl group such as phenyl; or the R groups can comprise amino groups such as aminoethyl, aminopropyl, aminoisobutyl, aminoethylaminopropyl, and aminoethylaminoisobutyl; provided at least one R group in the silane is an amino group.

Some representative examples of silanes containing amino groups which are suitable for use herein include aminomethyltriethylsilane, aminotrimethylsilane, (benzylmethylamino)triethylsilane, diethylaminomethyltrimethylsilane, diethylaminotrimethylsilane, diethylaminotriphenylsilane, diisopropylaminotrimethylsilane, dimethylaminotriethylsilane, dimethylaminotrimethylsilane, phenylmethylbis(dimethylamino)silane, tetrakis(dimethylamino)silane, tri-n-hexylsilylamine, trimethylaminosilane, triphenylaminosilane, tris(dimethylamino)ethylsilane, tris(dimethylamino)methylsilane, and tris(dimethylamino)phenylsilane.

Some examples of siloxanes with amino groups include those siloxane polymers and copolymers having number average molecular weights of 1,000-100,000, especially those having number average molecular weight of 5,000-50,000, such as aminopropyl terminated polydimethylsiloxanes and trimethylsilyl terminated dimethylsiloxane copolymers. The siloxanes should also contain 0.1-2.0 milliequivalents of amino functionality per gram of the siloxane on average, based on amino nitrogen of primary and secondary amino groups present in the siloxane. The amino groups may be present in the siloxane as aminoethyl groups, aminopropyl groups, aminoisobutyl groups, aminoethylaminopropyl groups, or aminoethylaminoisobutyl groups. Reference may be had to recently issued U.S. Pat. No. 6,475,974 (Nov. 5, 2002), for details of these and similar siloxanes containing amino groups, which can be used herein.

The Crosslinking Agent

The crosslinking agent for use herein is an organic epoxide containing at least two epoxy groups, i.e., diepoxide, including compositions such as ethylene glycol diglycidyl ether, diethylene glycol diglycidyl ether, polyethylene glycol diglycidyl ether, glycerine diglycidyl ether, triglycidyl ether, propylene glycol diglycidyl ether, butanediol diglycidyl ether; 1,2,3,4-diepoxybutane; 1,2,4,5-diepoxypentane; 1,2,5,6-diepoxyhexane; 1,2,7,8-diepoxyoctane; 1,3-divinylbenzene diepoxide; 1,4-divinylbenzene diepoxide; 4,4'-isopropylidene diphenol diglycidyl ether, and hydroquinone diglycidyl ether.

Other polyglycidyl ethers of alkane polyols, polyglycidyl ethers of poly(alkylene glycols), diepoxy alkanes, diepoxy aralkanes, and polyphenol polyglycidyl ethers, can also be used herein.

Two especially preferred organic epoxides containing at least two epoxy groups are shown below, in which n is a positive integer determining the molecular weight of the epoxide.

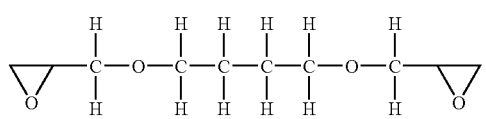

Butanediol Diglycidyl Ether

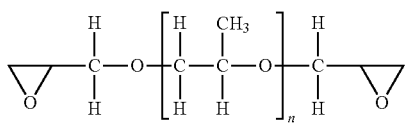

Poly(propylene glycol) Diglycidyl Ether

When it is desirable to use an epoxy functional silicone containing at least two epoxy groups instead of an organic epoxide containing at least two epoxy groups, a suitable epoxy functional silicone of the general structure shown below can be used, in which x represents an integer of one or more. If desired, epoxy functional silicones can be used which contain pendant epoxy groups along the silicone polymer chain.

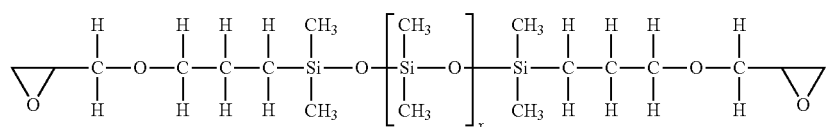

Epoxypropoxypropyl Terminated Polydimethylsiloxane

Such epoxy functional silicones are well known in the art and available commercially from sources such as the Dow Corning Corporation, Midland, Mich. USA. Typically, such silicones have a viscosity ranging from 1 to about 200 centistoke (mm$^2$/s) and molecular weights of about 300-6,000.

Chlorohydrins may be used in place of or in conjunction with the epoxides. As is know in the art, a chlorohydrin is a compound containing both chloro and hydroxyl radicals, and in some cases, chlorohydrin has been defined as compounds having the chloro and the hydroxy groups on adjacent carbon atoms, i.e.,

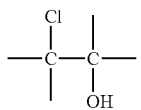

Chlorohydrins can be converted into epoxides by the action of a base. In the presence of the hydroxide ion, a small proportion of the alcohol exists as an alkoxide, which displaces the chloride ion from the adjacent carbon atom to produce a cyclic ether.

In addition, organic epoxides and epoxy functional silicones containing a single epoxy group can also be included as an optional component in order to control the cross link density and the overall molecular weight of the elastomers.

Other optional crosslinking agent comprises substituted di(meth)acrylates, unsubstituted di(meth)acrylates, and/or oligo(meth). Some examples of unsubstituted di(meth)acrylates are hexanediol diacrylate, butanediol diacrylate, 1,3-butanedioldimethacrylate, and neopentyl glycol diacrylate.

Some examples of substituted di(meth)acrylates are 1-acryloxy 2-hydroxy 3-methacryloxpropane, 2,2-dimethylpropyl 2,2-dimethylpropionate diacrylate, pentaerythritol diacrylate monostearate, polyethylene glycol-400 diacrylate, polyethylene glycol-300 diacrylate, polypropylene glycol-400 diacrylate, tetraethylene glycol diacrylate, polypropylene glycol-700 diacrylate, 2,2-bis[4-(acryloxydiethoxy)phenyl]propane, triethylene glycol diacrylate, tripropylene glycol diacrylate, polyethylene glycol-600 diacrylate, and propoxylated neopentyl glycol diacrylate.

An example of an unsubstituted oligo(meth)acrylate is trimethylolpropane triacrylate (TMPTA).

Some examples of substituted oligo(meth)acrylates are dipentacrythritol pentaacrylate and hexaacrylate, tetramethylolmethane triacrylate, trimethylolmethanol triacrylate, trimethylolpropane ethoxylate triacrylate, tris(acryloyloxyethyl) phosphate, tris(2-hydroxyethyl)isocyanurate triacrylate, ethoxylated trimethylolpropane triacrylate, propoxylated trimethylolpropane triacrylate, propoxylated glyceryl triacrylate, di(trimethylolpropane)tetraacrylate, di(pentaerythritol) pentaacrylate, and ethoxylated pentaerytiritol tetraacrylate.

Some examples of unsubstituted mono(meth)acrylates are methyl acrylate, ethyl acrylate, butyl acrylate, methyl methacrylate, cyclohexyl acrylate, isobornyl acrylate, lauryl acrylate, stearyl acrylate, ethylhexyl acrylate, tridecyl acrylate, isooctyl acrylate.

Some examples of substituted mono(meth)acrylates or related compounds are perfluoroalkylethyl acrylate, 2-acrylamido-2-methyl-1-propanesulfonic acid, 2-acryloyloxyethyl hydrogen phthalate, beta-acryloyloxyethyl hydrogen succinate, acryloyloxyethylphosphoric acid, 2-acryloyloxypropyl hydrogen phthalate, the potassium salt of (3-sulfopropyl)acrylate, the dipotassium salt of bis(3-sulfopropyl) itaconate, N,N-dimethyl-N-methacryloxaethyl-N-(3-sulfopropyl)ammonium betaine, 2-carboxyethyl acrylate, 2-hydroxyethyl acrylate, 2-ethylthioethyl methacrylate, acrylamide, methyl 2-acrylamido-2-methoxyacetate, acrylonitrile, (2-(acryl-oxy)ethyl)(4-benzenebenzyl)dimethylammonium bromide, (2-hydroxyethyl)acrylate, acryloxydimethylbutyrolactone, acrylic acid, methoxypolyethylene glycol-400 acrylate, nonylphenol ethoxylate acrylate, nonylphenol diethoxylate acrylate, phenoxydiethylene glycol acrylate, phenoxyethyl acrylate, dimethylaminoethyl acrylate, methyl chloride salt of dimethylaminoethyl acrylate, glycidyl acrylate, phenoxypolyethylene glycol acrylate, 2,2,3,3-tetrafluoropropyl acrylate, methoxypolyethylene glycol-1000 methacrylate, tetrahydrofurfuryl acrylate, caprolactone acrylate, 2(2-ethoxyethoxy)ethyl acrylate, 2-acrylamidoglycolic acid. Mixture of two or more diacrylates and/or oligoacrylates can also be used.

Some additional examples of crosslinking agents which can be used include hydroxyalkyl acrylates, examples of which are hydroxyethyl acrylate and hydroxyethyl methacrylate; as well as isocyanates such as hexamethylene diisocyanate.

The Surfactant

The surfactant may comprise a nonionic surfactant, a cationic surfactant, an anionic surfactant, an amphoteric surfactant, or a mixture of such surfactants.

Generally, the nonionic surfactant should be a non-silicon atom containing nonionic emulsifier. Most preferred are alcohol ethoxylates $R^4$—$(OCH_2CH_2)_aOH$, particularly fatty alcohol ethoxylates. Fatty alcohol ethoxylates typically contain the characteristic group —$(OCH_2CH_2)_aOH$ which is attached to fatty hydrocarbon residue $R^4$ which contains about eight to about twenty carbon atoms, such as lauryl ($C_{12}$), cetyl ($C_{16}$) and stearyl ($C_{18}$). While the value of "a" may range from 1 to about 100, its value is typically in the range of about 12 to about 40.

Some examples of suitable nonionic surfactants are polyoxyethylene (4) lauryl ether, polyoxyethylene (5) lauryl ether, polyoxyethylene (23) lauryl ether, polyoxyethylene (2) cetyl ether, polyoxyethylene (10) cetyl ether, polyoxyethylene (20) cetyl ether, polyoxyethylene (2) stearyl ether, polyoxyethylene (10) stearyl ether, polyoxyethylene (20) stearyl ether, polyoxyethylene (21) stearyl ether, polyoxyethylene (100) stearyl ether, polyoxyethylene (2) oleyl ether, and polyoxyethylene (10) oleyl ether. These and other fatty alcohol ethoxylates are commercially available under trademarks and tradenames such as ALFONIC®, BRIJ, GENAPOL®, NEODOL®, SURFONIC®, TERGITOL®, and TRYCOL. Ethoxylated alkylphenols can also be used, such as ethoxylated octylphenol, sold under the trademark TRITON®.

Cationic surfactants useful in the invention include compounds containing quaternary ammonium hydrophilic moieties in the molecule which are positively charged, such as quaternary ammonium salts represented by $R'R''R'''R''''N^+X^-$ where R', R'', R''', and R'''' are alkyl groups containing 1-30 carbon atoms, or alkyl groups derived from tallow, coconut oil, or soy; and X is halogen, i.e., chlorine or bromine. Most preferred are dialkyldimethyl ammonium salts represented by $R'R''N^+(CH_3)_2X^-$, where R' and R'' are alkyl groups containing 12-30 carbon atoms, or alkyl groups derived from tallow, coconut oil, or soy; and X is halogen. Monoalkyltrimethyl ammonium salts can also be employed, and are represented by $R'N^+(CH_3)_3X^-$ where R' is an alkyl group containing 12-30 carbon atoms, or an alkyl group derived from tallow, coconut oil, or soy; and X is halogen.

Some representative quaternary ammonium salts are dodecyltrimethyl ammonium bromide (DTAB), didodecyldimethyl ammonium bromide, dihexadecyldimethyl ammonium chloride, dihexadecyldimethyl ammonium bromide, dioctadecyldimethyl ammonium chloride, dieicosyldimethyl ammonium chloride, didocosyldimethyl ammonium chloride, dicoconutdimethyl ammonium chloride, ditallowdimethyl ammonium chloride, and ditallowdimethyl ammonium bromide. These and other quaternary ammonium salts are commercially available under tradenames such as ADOGEN, ARQUAD, TOMAH, and VARIQUAT.

Among the various types of anionic surfactants which can be used are sulfonic acids and their salt derivatives; alkali metal sulfosuccinates; sulfonated glyceryl esters of fatty acids such as sulfonated monoglycerides of coconut oil acids; salts of sulfonated monovalent alcohol esters such as sodium oleyl isothionate; amides of amino sulfonic acids such as the sodium salt of oleyl methyl tauride; sulfonated products of fatty acid nitriles such as palmitonitrile sulfonate; sulfonated aromatic hydrocarbons such as sodium alpha-naphthalene monosulfonate; condensation products of naphthalene sulfonic acids with formaldehyde; sodium octahydro anthracene sulfonate; alkali metal alkyl sulfates such as sodium lauryl (dodecyl) sulfate (SDS); ether sulfates having alkyl groups of eight or more carbon atoms; and alkylaryl sulfonates having one or more alkyl groups of eight or more carbon atoms.

Some examples of commercial anionic surfactants useful in this invention include triethanolamine linear alkyl sulfonate sold under the tradename BIO-SOFT N-300 by the Stepan Company, Northfield, Ill.; sulfates sold under the tradename POLYSTEP by the Stepan Company; and sodium n-hexadecyl diphenyloxide disulfonate sold under the tradename DOWFAX 8390 by The Dow Chemical Company, Midland, Mich.

Amphoteric surfactants can also be used which generally comprise surfactant compositions such as alkyl betaines, alkylamido betaines, and amine oxides, specific examples of which are known in the art.

The Aqueous Polar Phase

The aqueous polar phase used in the process is water, or an aqueous phase containing water and a polar solvent.

The polar solvents especially preferred herein are those compounds determined to be cosmetically acceptable non-aqueous polar solvents, among which are monohydroxy alcohols such as ethyl alcohol and isopropyl alcohol; diols and triols such as propylene glycol, 1,2-hexanediol $CH_3(CH_2)_3CH(OH)CH_2OH$, 2-methyl-1,3-propane diol $HOCH_2CH(CH_3)CH_2OH$, and glycerol; glycerol esters such as glyceryl triacetate (triacetin), glyceryl tripropionate (tripropionin), and glyceryl tributyrate (tributyrin); and polyglycols such as polyethylene glycols and polypropylene glycols among which are PPG-14 butyl ether $C_4H_9[OCH(CH_3)CH_2]_{14}OH$. In applications other than personal care, these and other non-aqueous polar solvents can be employed.

The aqueous polar phase of the emulsion or microemulsion therefore, can consist of water, or a mixture of water and a polar solvent which is preferably a polar organic compound. Generally, this component will be present in the composition in an amount to provide the balance of the composition to 100 percent, after taking in account the amounts of the other components used in formulating a suitable composition. Typically, however, this component will comprise 0.1-99.8 percent by weight based on the total weight of the O/W or W/O emulsion or microemulsion composition, preferably 10-95 percent by weight. While mixtures of liquids can be used to form this single phase component of the composition, liquids should be miscible and capable of forming an essentially homogeneous mixture.

Optional Components

Since emulsions and microemulsions are susceptible to microbiological contamination, a preservative may be required as an optional component of the composition, and some representative compounds which can be used include formaldehyde, salicylic acid, phenoxyethanol, DMDM hydantoin (1,3-dimethylol-5,5-dimethyl hydantoin), 5-bromo-5-nitro-1,3-dioxane, methyl paraben, propyl paraben, sorbic acid, imidazolidinyl urea sold under the name GERMALL® II by Sutton Laboratories, Chatham, N.J., sodium benzoate, 5-chloro-2-methyl-4-isothiazolin-3-one sold under the name KATHON CG by Rohm & Haas Company, Philadelphia, Pa., and iodopropynl butyl carbamate sold under the name GLYCACIL® L by Lonza Incorporated, Fair Lawn, N.J.

A freeze/thaw stabilizer can be included as another optional component of the composition including compounds such as ethylene glycol, propylene glycol, glycerol, trimethylene glycol, and polyoxyethylene ether alcohols such as RENEX 30 sold by ICI Surfactants, Wilmington, Del.

Another optional component of the composition which can be included is a corrosion inhibitor such as an alkanolamine, an inorganic phosphate such as zinc dithiophosphate, an inorganic phosphonate, an inorganic nitrite such as sodium nitrite, a silicate, a siliconate, an alkyl phosphate amine, a succinic anhydride such as dodecenyl succinic anhydride, an amine succinate, or an alkaline earth sulfonate such as sodium sulfonate or calcium sulfonate.

An additional optional component which can be used are low molecular weight polysiloxanes such as low molecular weight linear or cyclic volatile methyl siloxanes, or low molecular weight linear and cyclic volatile and non-volatile alkyl and aryl siloxanes. Most preferred, are low molecular weight linear and cyclic volatile methyl siloxanes. These compositions are well known in the art and reference may be had to U.S. Pat. No. 6,238,657 (May 29, 2001), for numerous specific examples of suitable compositions.

Alternate Components

When O/W or W/O emulsion or microemulsion compositions according to this invention are used in particular product(s) intended for the personal care market, the compositions may be formulated to include one or more alternate components, for example:

(A) conditioning agents such as cationic polymers, proteins, natural oils, elastomeric silanes and siloxanes containing nitrogen atoms, hydrocarbons other than waxes, and mixtures thereof;
(B) cosurfactants such as betaines, monoalkylalkanolamides, dialkylalkanolamides, amine oxides, amine glycinates, amine propionates, amine sultaines, and mixtures thereof;
(C) polyhydric alcohols such as glycerin and sorbitol.

Products containing alternate components (A) are especially useful as conditioners, products containing (A) and (B) are especially useful as shampoos, and products containing (C) are especially useful as moisturizers.

Some examples of additional alternate components which can be included in personal care products containing the emulsion or microemulsion compositions are suspending agents and thickeners.

A suspending agent can be used at concentrations effective for suspending the silicone component of the emulsion or microemulsion composition or other water-insoluble material in dispersed form, in the personal care product. Such suspending agents can include crystalline suspending agents which are categorized as acyl derivatives, long chain amine oxides, and mixtures thereof. These suspending agents include ethylene glycol esters of fatty acids, preferably having 16-22 carbon atoms. Specific examples include polyacrylic acids, crosslinked polymers of acrylic acid, copolymers of acrylic acid with a hydrophobic monomer, copolymers of carboxylic acid-containing monomers and acrylic esters, crosslinked copolymers of acrylic acid and acrylate esters, heteropolysaccharide gums, and crystalline long chain acyl derivatives. The long chain acyl derivative are preferably ethylene glycol stearates, alkanolamides of fatty acids having 16-22 carbon atoms, or mixtures thereof.

Thickeners can be used to facilitate the hand application of the personal care product to the hair, skin or other substrate, and are added in sufficient quantities to provide a more luxurious effect. Representative thickening agents sodium alignate; gum arabic; guar gum; hydroxypropyl guar gum; cellulose derivatives such as methylcellulose, hydroxypropyl methylcellulose, hydroxyethylcellulose, and hydroxypropylcellulose; starch and starch derivatives such as hydroxyethylamylose and starch amylose; locust bean gum; electrolytes such as sodium chloride and ammonium chloride; saccharides such as fructose and glucose; and derivatives of saccharides such as PEG-120 methyl glucose dioleate.

Other alternate components for hair care and skin care products include fragrances, vitamins, ceramides, amino-acid derivatives, liposomes, and botanicals and/or plant extracts. Other alternate components depending upon the particular use of the personal care product include glycols, vitamins A and E in their various forms, sunscreen agents, humectants, emollients, occlusive agents, and esters. Other alternate components may be added to the personal care products containing the emulsion and microemulsion compositions of the invention, such as colorants, electrolytes, pH control agents, foam boosters and foam builders, foam stabilizers, antimicrobials, antioxidants, ultraviolet light absorbers, and medicaments. In particular, such alternate components can be used in amounts of 0.1-5 parts by weight per 100 parts by weight of conditioning shampoo products, preferably 0.1-1 part by weight per 100 parts by weight.

Preparation

The amount of each of the various components used in preparing emulsions and microemulsions according to the invention, based on the total weight of the composition, is:
(i) 0.01-90 percent by weight of the organic quaternary ammonium compound having epoxide groups or halohydrin groups in its molecule;
(ii) 0.01-90 percent by weight of the silane or the siloxane having amino groups in its molecule;
(iii) 0.01-90 percent by weight of the crosslinking agent;
(iv) 0.01-90 percent by weight of the surfactant, preferably 240 percent by weight, more preferably 5-20 percent by weight; and
(v) the balance to 100 percent by weight being the aqueous polar phase. Emulsions and microemulsions can also be prepared by omitting component (i), i.e., the organic quaternary ammonium compound having epoxide groups or halohydrin groups in its molecule;

If an optional component is included, it is generally present in an amount of 0.01-0.1 percent by weight of each optional component, i.e., preservative, freeze/thaw stabilizer, or corrosion inhibitor.

The reaction can be made to take place by simply mixing all of the components together, and this is the minimum requirement to obtain reaction, i.e., to perform the "reacting"

step under the circumstances. However, it is generally preferred to mix all of the reactants together and to heat them. A catalyst is typically not necessary but under some circumstance, an appropriate catalyst may be employed. In this regard, it has been found that in general, tertiary amines do not add readily to epoxides. This can be improved if the reaction mixture is acidified, especially in stoichiometric proportions, or the tertiary amine is pretreated with an acid in order to convert it to its acid salt.

The emulsions and microemulsions can be prepared using simple propeller mixers, turbine-type mixers, Brookfield counter-rotating mixers, or homogenizing mixers. No special equipment or processing conditions are generally required.

The following examples are set forth in order to illustrate the invention in more detail. The Examples 1 and 2 below are representative of the procedures used to prepare several emulsions as shown in Table 1.

EXAMPLE 1

Into a reaction vessel was placed 200 gram of a trimethylsiloxy terminated amino functional siloxane having a degree of polymerization (DP) of about 300, and containing about 2 mole percent of aminoethyl aminoisobutyl methyl siloxane groups. 30 gram of Tergitol TMN-6 and 30 gram of Tergitol TMN-10 nonionic surfactants were added, and mixed with a mechanical stirrer for a period of ten to fifteen minutes. 40 gram of water and 0.37 gram of glacial acetic acid were then added to the solution, and allowed to mix for thirty minutes. After mixing, the solution was heated to 75±5° C., and 13.6 gram of glycidyltrimethylammonium chloride (GTMAC) was added. This mixture was stirred for two hours at 75±5° C. Then, 320 gram of water was quickly added to the solution, and mixed rapidly for one hour. An additional 114 gram of water was added, and mixed for thirty minutes. At this time, 6.5 gram of trimethylolpropane triacrylate (TMPTA) was added to crosslink the amino functional siloxane (AFS). This solution was held at 75±5° C. for two hours with stirring. The emulsion was then allowed to cool to room temperature. The final product was a clear emulsion with a visible blue tint containing an elastomeric quaternary ammonium functional siloxane (EQAFS).

EXAMPLE 2

Into a reaction vessel was placed 200 gram of a trimethylsiloxy terminated amino functional siloxane with a DP of about 300, and containing about 2 mole percent of aminoethyl aminoisobutyl methyl siloxane groups. 30 gram of Tergitol TMN-6 and 30 gram of Tergitol TMN-10 nonionic surfactants were added, and mixed with a mechanical stirrer for a period of ten to fifteen minutes. 40 gram of water and 0.37 gram of glacial acetic acid were added to the solution, and then mixed for thirty minutes. Then 320 gram of water was quickly added to the solution, and mixed rapidly for one hour. An additional 114 gram of water was added, and mixed for thirty minutes. At this time, 14.6 gram of a trimethylsiloxy terminated siloxane having a DP of about 5, and containing three methyl (propyl-3-glycidoxy) siloxane groups, was added to crosslink the amino functional siloxane (AFS). This solution was held at 75±5° C. for two hours with stirring. The emulsion was then allowed to cool to room temperature. The final product was a clear emulsion with a visible blue tint containing an elastomeric amine functional siloxane (EAFS)

Example 2 illustrates another method which can be used, if desired, for making oil-in-water (O/W) and water-in-oil (W/O) emulsions and microemulsions containing elastomeric silanes or siloxanes having nitrogen atoms as the oil phase of the emulsions or microemulsions. It essentially involves the sequential steps of:

(i) preparing a first mixture containing only silanes or siloxanes having amino groups in their molecule and a surfactant;

(ii) preparing a second mixture by adding a first portion of an aqueous polar phase to the first mixture;

(iii) preparing a third mixture by adding the balance of the aqueous polar phase to the second mixture;

(iv) preparing a fourth mixture by adding a crosslinking agent to the third mixture; and (v) heating the fourth mixture.

TABLE 1

| | Emulsion Compositions | | | | | | |
|---|---|---|---|---|---|---|---|
| Emulsion | AFS Reacted with TMPTA crosslinker (%) | AFS Reacted with siloxane crosslinker (%) | AFS Reacted with GTMAC (%) | TMN-6 (%) | TMN-10 (%) | EQAFS/ EAFS in Emulsion (%) | Particle Size (μm) |
| Emulsion 1 | 33.0 | — | 0 | 4 | 4 | 28 | 0.022 |
| Emulsion 2 | 33.0 | — | 0 | 4 | 4 | 28 | 0.325 |
| Emulsion 3 | 33.0 | — | 33 | 4 | 4 | 28 | 0.048 |
| Emulsion 4 | 16.5 | — | 33 | 4 | 4 | 28 | 0.035 |
| Emulsion 5 | — | 33.0 | 0 | 4 | 4 | 28 | 0.026 |
| Emulsion 6 | — | 16.5 | 0 | 4 | 4 | 28 | 0.030 |
| Emulsion 7 | — | 33.0 | 33 | 4 | 4 | 28 | 0.096 |
| Emulsion 8 | — | 16.5 | 33 | 4 | 4 | 28 | 0.036 |

EXAMPLE 3

Hair Conditioner Formulations

Samples of elastomeric siloxane containing emulsions were added to rinse-off conditioning formulations using about two percent by weight of the elastomeric siloxane. The conditioning formulations are shown in Table 2. In the table, Conditioner A contained no silane or siloxane. Conditioners B, C, D, and E contained different elastomeric siloxane containing emulsions, with an acrylate crosslinker, according to the present invention. Conditioner F contained a non-elastomeric amine functional siloxane emulsion for comparison.

TABLE 2

| Ingredient | Conditioner A Weight Percent | Conditioner B Weight Percent | Conditioner C Weight Percent | Conditioner D Weight Percent | Conditioner E Weight Percent | Conditioner F Weight Percent |
|---|---|---|---|---|---|---|
| Deionized Water | q.s. to 100% | q.s. to 100% | q.s. to 100% | q.s. to 100% | q.s. to 100% | q.s. to 100% |
| Hydroxyethylcellulose | 1.5 | 1.5 | 1.5 | 1.5 | 1.5 | 1.5 |
| Cetearyl Alcohol | 1.0 | 1.0 | 1.0 | 1.0 | 1.0 | 1.0 |
| PEG-100 Stearate & Glyceryl Stearate | 1.0 | 1.0 | 1.0 | 1.0 | 1.0 | 1.0 |
| Siloxane of Emulsion 1 | — | 2.0 | — | — | — | — |
| Siloxane of Emulsion 2 | — | — | 2.0 | — | — | — |
| Siloxane of Emulsion 3 | — | — | — | 2.0 | — | — |
| Siloxane of Emulsion 4 | — | — | — | — | 2.0 | — |
| Amino Siloxane Emulsion | — | — | — | — | — | 2.0 |
| DMDM Hydantoin | 0.2 | 0.2 | 0.2 | 0.2 | 0.2 | 0.2 |

In Table 2, the four ingredients hydroxyethylcellulose, cetearyl alcohol, PEG-100 stearate & glyceryl stearate, and DMDM hydantoin, were delivered in the forms of Natrosol® 250 MR sold by Hercules Incorporated, Wilmington, Del.; Lanette O sold by Cognis Corporation, Hoboken, N.J.; Arlacel® 165 sold by Uniqema (ICI Surfactants), Wilmington, Del.; and Glydant® sold by Lonza Incorporated, Fairlawn, N.J., respectively.

The amount of elastomeric siloxane was present in Conditioners B-E at a concentration based on level of siloxane active in the conditioner. The amino siloxane emulsion was used for comparison and comprised a commercially available cationic emulsion containing about 35 percent of an amine-functional silicone polymer, which is used for providing conditioning benefits to the hair. The amount of amino siloxane was also based on level of siloxane active in the conditioner.

Procedure—Preparation of Hair Sample

Slightly bleached European human hair from International Hair Importer and Products, Inc., was used for testing the conditioners prepared herein. A master hand of hair about eight inches in length was subdivided into a series of individual hair tresses. Each tress weighed about 2.5 grams. A 0.5 inch (1.27 cm) of the root end of the hair was trimmed and glued to a 2 inch by 2 inch (5.08 cm by 5.08 cm) plastic tab using DUCO CEMENT®. The cement was allowed to dry, and the hair tress was combed and trimmed to a length such that six inches (15.24 cm) of hair extended below the bottom of the plastic tab. A hole was punched in middle of tab about one fourth inch (0.635 cm) from its top. Each tress was rinsed for 15 seconds under 40° C. tap water. Using a pipette, 1.0 gram of a solution containing nine percent of sodium lauryl sulfate was applied and lathered through the tress for 30 seconds. The tress was rinsed for 30 seconds under running water. Excess water was removed from the tress by passing the tress between the index and middle fingers of the hand. The tresses were placed on a tray covered with paper towels and dried overnight. Each tress was hand combed three times with the narrow teeth of an ACE® comb, and evaluated using INSTRON WET and INSTRON DRY COMBING procedures.

INSTRON procedures are standard, recognized, and industrially acceptable protocols, see for example, U.S. Pat. No. 5,389,364 (Feb. 14, 1995), U.S. Pat. No. 5,409,695 (Apr. 25, 1995), U.S. Pat. No. 5,419,627 (May 30, 1995), and U.S. Pat. No. 5,504,149 (Apr. 2, 1996).

For tests involving rinse-off conditioners, hair tresses are rinsed with tap water for 30 seconds at 40° C. The test conditioner is applied to the tress in the amount of 0.8 gram, and the tress is stroked for 30 seconds. The tress is rinsed for 30 seconds under tap water at 40° C. Excess water is removed by pulling the tress through the index and middle fingers of the hand. The tresses are allowed to dry separately on a paper towel overnight at room temperature. The tresses are combed once before performing an INSTRON study.

Test Procedure

INSTRON COMBING is an industry recognized test for determining hair conditioning by the ease of wet combing and the ease of dry combing. The test employs an INSTRON strain gauge, which is equipped to measure the force required to comb the hair. The conditioning performance is based on the ability of a particular hair treatment formulation, such as a shampoo or a hair conditioner, to reduce the force required to comb the hair with the INSTRON strain gauge. The force is reported as an Average Combing Load (ACL). The lower the number of the ACL value, the better is the conditioning effect imparted by the formulation being tested. Typically, ACL baselines are initially established using untreated tresses that have only been washed with a sodium lauryl sulfate solution. The effectiveness of a treatment can then be expressed as an ACL of the treated tress or percent reduction in ACL, calculated using the relationship:

(untreated hair ACL-treated hair ACL)×100 divided by the untreated hair ACL

According to the INSTRON WET COMBING method, hair is first wetted by dipping it into distilled water, and then the hair is detangled by combing the tress three times. The tress is then retangled by dipping in distilled water three times. Excess water is removed by passing the tress through the index and middle fingers of the hand twice. The tress is placed on a hanger and INSTRON combed. Retangling and INSTRON combing are repeated until all data points are collected. An average combing force of three tresses is measured for each treatment.

The results of INSTRON WET COMBING using Conditioners B-E according to the present application are shown in Table 3. It can be seen that the elastomeric quaternary ammonium functional siloxane containing emulsions, i.e., Conditioner D and E, provided the largest reduction in wet combing forces, compared to (i) control Conditioner A which contained no silane or siloxane, and (ii) Conditioners B and C which contained amino functional siloxane elastomeric emulsions without quaternary ammonium functionality. Conditioner E also outperformed amino functional silicone emulsion containing conditioner (F). All of the conditioners containing the elastomeric siloxane containing emulsions are therefore capable of improving the wet conditioning properties of hair.

According to the INSTRON DRY COMBING method, hair is detangled by combing the tress 3 times. Then hair is retangled by swirling the tress clockwise 3 times and swirling it counter clockwise 3 times. The tress is then placed on a hanger and INSTRON combed. Retangle and Instron combing are repeated until all data points are collected. An average combing force for three tresses is measured for each treatment.

G, H, I and J contained different elastomeric siloxane containing emulsions using an epoxy functional silicone cross linking agent according to the present invention. Conditioner F contained a non-elastomeric amine functional siloxane emulsion for comparison

TABLE 5

| Ingredient | Conditioner A Weight % | Conditioner G Weight % | Conditioner H Weight % | Conditioner I Weight % | Conditioner J Weight % | Conditioner F Weight % |
|---|---|---|---|---|---|---|
| Deionized Water | q.s. to 100% | q.s. to 100% | q.s. to 100% | q.s. to 100% | q.s. to 100% | q.s. to 100% |
| Hydroxyethylcellulose | 1.5 | 1.5 | 1.5 | 1.5 | 1.5 | 1.5 |
| Cetearyl Alcohol | 1.0 | 1.0 | 1.0 | 1.0 | 1.0 | 1.0 |
| PEG-100 Stearate & Glyceryl Stearate | 1.0 | 1.0 | 1.0 | 1.0 | 1.0 | 1.0 |
| Siloxane of Emulsion 5 | — | 2.0 | — | — | — | — |
| Siloxane of Emulsion 6 | — | — | 2.0 | — | — | — |
| Siloxane of Emulsion 7 | — | — | — | 2.0 | — | — |
| Siloxane of Emulsion 8 | — | — | — | — | 2.0 | — |
| Amino Siloxane Emulsion | — | — | — | — | — | 2.0 |
| DMDM Hydantoin | 0.2 | 0.2 | 0.2 | 0.2 | 0.2 | 0.2 |

The results of INSTRON DRY COMBING tests conducted with Conditioners A-F are shown in Table 4. Table 4 shows that the elastomeric siloxane containing emulsions of the present invention provide a significant reduction in dry combing forces, compared to control Conditioner A, and that they are comparable to comparison Conditioner F containing the non-elastomeric amino functional silicone emulsion. All of the conditioners containing the elastomeric siloxane containing emulsions are therefore capable of improving the dry conditioning properties of hair.

TABLE 3

INSTRON WET COMBING

| Conditioner | ACL Reduction, Percent |
|---|---|
| A | 0 |
| B | 53 |
| C | 78 |
| D | 87 |
| E | 93 |
| F | 81 |

TABLE 4

INSTRON DRY COMBING

| Conditioner | ACL Reduction, Percent |
|---|---|
| A | -10 |
| B | 31 |
| C | 45 |
| D | 45 |
| E | 51 |
| F | 44 |

EXAMPLE 4

Hair Conditioner Formulations

Samples of elastomeric siloxane containing emulsions were added to rinse-off conditioning formulations using about two percent by weight of the elastomeric siloxane. The conditioning formulations are shown in Table 5. In the table, Conditioner A contained no silane or siloxane. Conditioners The results of INSTRON WET COMBING using Conditioners G-J according to the present application are shown in Table 6. It can be seen that the elastomeric siloxane containing emulsions, i.e., Conditioner I and Conditioner J, provided the largest reduction in wet combing forces compared to control Conditioner A containing no silane or siloxane, and Conditioners G and H which contained the amino elastomer siloxane emulsions without quaternary ammonium functionality. Conditioners I and J also outperformed the non-elastomeric amino functional silicone emulsion containing conditioner (F). All of the conditioners containing the elastomeric siloxane containing emulsions are therefore capable of improving the wet conditioning properties of hair.

The results of INSTRON DRY COMBING tests conducted with Conditioners A, G-J and F are shown in Table 4. Table 4 shows that the elastomeric siloxane containing emulsions of the present invention provide a reduction in dry combing forces, compared to control Conditioner A containing no silane or siloxane, and are comparable to comparison Conditioner F which contained a non-elastomeric amino functional silicone emulsion. All of the conditioners containing the elastomeric siloxane containing emulsions are therefore capable of improving the dry conditioning properties of hair.

TABLE 6

INSTRON WET COMBING

| Conditioner | ACL Reduction, Percent |
|---|---|
| A | 0 |
| G | 62 |
| H | 76 |
| I | 86 |
| J | 94 |
| F | 81 |

TABLE 7

INSTRON DRY COMBING

| Conditioner | ACL Reduction, Percent |
|---|---|
| A | -10 |
| G | 34 |
| H | 47 |

TABLE 7-continued

INSTRON DRY COMBING

| Conditioner | ACL Reduction, Percent |
|---|---|
| I | 33 |
| J | 36 |
| F | 44 |

EXAMPLE 5

Hair Conditioner Formulations

Rinse-off conditioners having the following composition were prepared:

TABLE 8

| Ingredient | Conditioner J Weight Percent | Conditioner K Weight Percent | Conditioner L Weight Percent | Conditioner M Weight Percent |
|---|---|---|---|---|
| Deionized Water | q.s. to 100% | q.s. to 100% | q.s. to 100% | q.s. to 100% |
| Hydroxyethyl-cellulose | 1.5 | 1.5 | 1.5 | 1.5 |
| Cetearyl Alcohol | 1.0 | 1.0 | 1.0 | 1.0 |
| PEG-100 Stearate & Glyceryl Stearate | 1.0 | 1.0 | 1.0 | 1.0 |
| Siloxane of Emulsion 8 | 2.0 | — | — | — |
| Siloxane of Emulsion 8 | — | 1.0 | — | — |
| Siloxane of Emulsion 8 | — | — | 0.5 | — |
| Siloxane of Emulsion 8 | — | — | — | 0.25 |
| DMDM Hydantoin | 0.2 | 0.2 | 0.2 | 0.2 |

INSTRON combing was performed as in Example 3 using conditioners J, K, L, and M shown above. The results are shown in Tables 9 and 10 indicating that the elastomeric quaternary ammonium functional siloxane containing emulsions tested at concentrations as low as 0.25% in the rinse-off conditioner formulation, still provided a significant reduction in wet and dry combing forces, thereby improving the conditioning properties of hair.

TABLE 9

INSTRON WET COMBING

| Conditioner | ACL Reduction, Percent |
|---|---|
| J | 91 |
| K | 90 |
| L | 80 |
| M | 82 |

TABLE 10

INSTRON DRY COMBING

| Conditioner | ACL Reduction, Percent |
|---|---|
| J | 43 |
| K | 46 |

TABLE 10-continued

INSTRON DRY COMBING

| Conditioner | ACL Reduction, Percent |
|---|---|
| L | 30 |
| M | 52 |

EXAMPLE 6

Hair Shampoo Formulation

Shampoo compositions were prepared containing the ingredients shown in the following Table.

TABLE

Example 6

| Ingredient | Shampoo A (Weight %) | Shampoo B (Weight %) | Shampoo C (Weight %) |
|---|---|---|---|
| Deionized Water | q.s. to 100% | q.s. to 100% | q.s. to 100% |
| Sodium Laureth Sulfate | 30 | 30 | 30 |
| Cocamide DEA | 3.0 | 3.0 | 3.0 |
| PEG-150 Pentaerythrityl Tetrastearate | 1.5 | 1.5 | 1.5 |
| Cocamidopropyl Betaine | 7.0 | 7.0 | 7.0 |
| Siloxane of Emulsion 1 | 2.0 | — | — |
| Siloxane of Emulsion 2 | — | 2.0 | — |
| Siloxane of Emulsion 4 | — | — | 2.0 |
| DMDM Hydantoin | 0.2 | 0.2 | 0.2 |

In the above Table for Example 6, the five ingredients sodium lauryl sulfate, cocamide DEA, PEG-150 pentaerythrityl tetrastearate, cocamidopropyl betaine, and DMDM hydantoin were delivered in the form of Standapol ES-3, 30% active, sold by Cognis Corporation, Hoboken, N.J.; Calamide C sold by Pilot Chemical Corporation, Santa Fe Springs, Calif.; Crothix sold by Croda Incorporated, Parsippany, N.J.; Monateric CAB, 30% active, sold by Uniqema (ICI Surfactants), Paterson, N.J.; and Glydant® sold by Lonza Incorporated, Fairlawn, N.J., respectively.

Deionized water was added to a mixing vessel and heated to 65° C. Using moderate agitation, the PEG-150 pentaerythrityl tetrastearate was completely dispersed. The heat was turned off and sodium laureth sulfate, Cocamide DEA, and cocamidopropyl betaine were added. When the temperature was less than 40° C., the elastomeric siloxane containing emulsion was added. The shampoo was mixed for 5 to 10 minutes and then DMDM hydantoin was added. Water loss was compensated, and the formulation was mixed for an additional 5 minutes. The final pH of the shampoo formulations was between 6 to 7.

Test Procedure

CURL RETENTION is an industry recognized test for determining hair styling and hold properties by subjecting curled hair tresses to constant temperature and humidity conditions for a specified period of time. Curl retention is measured by recording the difference in length of curled hair tresses before and during high humidity and constant temperature conditions. Already prepared natural virgin brown round hair tresses weighing 2 gram and measuring 25 cm long are employed. To pre-treat all of the tresses, 1.0 gram of a solution containing nine percent of sodium lauryl sulfate is applied and lathered through each tress for 30 seconds. Each tress is rinsed for 30 seconds under running water. Excess water is removed from each tress by passing the tress between the index and middle fingers of the hand. The tresses are placed on a tray covered with paper towels and dried overnight. Each tress is hand combed three times with the narrow teeth of a comb. Each tress is then wet for 15 seconds under tap water at 37° C. and the excess water is removed by pulling the tress through the index and middle fingers of the hand.

Then each of the tresses is treated with either 500 microliters of a 6% active silicone emulsion or 2% active silicone mousse formulation. Each tress is curled around a ¼" spiral perm rod and dried in a 40° C. oven overnight. The tresses are removed from the rod, keeping the curl intact and hung in a humidity chamber. The conditions of the humidity chamber are 25° C. and 70% relative humidity. The tress lengths are then measured periodically over 5 hours. Following the test, the maximum tress length is measured by unrolling it completely. The percent curl retention is calculated using the relationship:

(maximum tress length−tress length at specific time)/
(maximum tress length−tress length at time=0)×
100

An average of two tresses is measured for each treatment. The Instron combing and curl retention results for the shampoo formulations of Example 6 are shown in Tables 11 and 12.

TABLE 11

| | INSTRON COMBING | |
|---|---|---|
| Shampoo | Wet ACL Reduction, Percent | Dry ACL Reduction, Percent |
| B | 12 | 25 |

TABLE 12

| CURL RETENTION | |
|---|---|
| Shampoo | % Curl Retention after 5 hrs |
| Water | 31 |
| A | 38 |
| C | 36 |

These results show that the shampoos containing the elastomeric siloxane containing emulsions are useful for cleansing and conditioning the hair and for providing a flexible styling benefit.

EXAMPLE 7

Mousse Formulation

An aqueous mousse composition was prepared from the ingredients shown in the Table below using a conventional mixing technique.

TABLE

| | Example 7 | |
|---|---|---|
| Ingredient | Mousse A (Weight %) | Mousse B (Weight %) |
| Deionized Water | q.s. to 100% | q.s. to 100% |
| Polyquaternium-11 | 8 | 8 |
| Oleth-20 | 0.56 | 0.56 |
| Siloxane of Emulsion 6 | — | 2.0 |
| DMDM Hydantoin | 0.2 | 0.2 |

In the above Table, the three ingredients polyquaternium-11, oleth-20, and DMDM hydantoin were delivered in the form of Gafquat® 755N, 20% active, sold by ISP Technologies Incorporated, Wayne, N.J.; Volpo 20 sold by Croda Incorporated, Parsippany, N.J.; and Glydant® sold by Lonza Incorporated, Fairlawn, N.J., respectively.

TABLE 13

| CURL RETENTION | |
|---|---|
| Mousse | % Curl Retention after 5 hrs |
| Control | 45 |
| Emulsion 6 | 50 |

The curl retention test results shown in Table 13 indicate that the mousse containing Emulsion 6, an elastomeric amine functional emulsion, is useful for conditioning hair and for providing additional flexible styling and hold benefits, compared to the Control mousse formulation which contained no elastomeric siloxane.

EXAMPLE 8

Leave-on Conditioner Application

Emulsions 1-8 of this invention were further diluted to a 6% active concentration of the elastomeric siloxane, and 500 microliter of each of the diluted emulsions was applied to hair tresses for curl retention testing. The curl retention results are shown below in Tables 14 and 15.

TABLE 14

| CURL RETENTION | |
|---|---|
| Dilute Emulsion | % Curl Retention after 5 hrs |
| Emulsion 1 | 49 |
| Emulsion 2 | 49 |
| Emulsion 3 | 52 |
| Emulsion 4 | 50 |
| Siloxane Resin | 48 |
| Water | 31 |

TABLE 15

| CURL RETENTION | |
|---|---|
| Dilute Emulsion | % Curl Retention after 5 hrs |
| Emulsion 5 | 44 |
| Emulsion 6 | 47 |
| Emulsion 7 | 48 |
| Emulsion 8 | 50 |
| Water | 26 |

The results in Tables 14 and 15 show that the elastomeric siloxane containing emulsions provide flexible hold and styling benefits, in addition to imparting a nice soft feel to the hair. Even when the tresses were stretched or combed to remove the curl, they were observed to bounce right back to their original shaped curl. These results show that the curl retention properties are similar to those obtained using commercial siloxane based resins. However, conditioning properties such as combing and feel are significantly better when using the elastomeric siloxane containing emulsions.

The emulsions and microemulsions prepared herein are useful in personal care, for example, in preparing compositions such as antiperspirants and deodorants. They can be used in skin creams, skin care lotions, moisturizers, facial treatments such as acne or wrinkle removers, personal and facial cleansers, bath oils, perfumes, colognes, sachets, sunscreens, pre-shave and after-shave lotions, shaving soaps, and shaving lathers. They can be used in hair shampoos, hair conditioners, hair colorants, hair relaxers, hair sprays, mousses, permanents, depilatories, and cuticle coats. In cosmetics, the compositions can be added to make-ups, color cosmetics, foundations, blushes, lipsticks, eyeliners, mascara, oil removers, color cosmetic removers, and powders. In such applications, the compositions may include oil soluble, polar solvent soluble, and water soluble ingredients such as vitamins.

The emulsions and microemulsions are also capable of functioning as carriers for pharmaceuticals, biocides, and other biologically active substances; and such compositions have utility as additives for cellulosic or synthetic nonwoven carrier substrates used in wet-like cleansing wipes such as wet-wipes, tissues, and towels, marketed generally for personal hygiene and household cleaning tasks.

Other variations may be made in compounds, compositions, and methods described herein without departing from the essential features of the invention. The embodiments of the invention specifically illustrated herein are exemplary only and not intended as limitations on their scope except as defined in the appended claims.

The invention claimed is:

1. A method of treating hair, skin, or the underarm comprising applying to hair, skin, or the underarm, an oil-in-water (O/W) or water-in-oil (W/O) emulsion or microemulsion composition containing an elastomeric silane or siloxane having quaternary ammonium groups in its molecule as the oil phase of the emulsion or microemulsion, prepared by reacting (i) an organic quaternary ammonium compound having epoxide groups or halohydrin groups in its molecule, with (ii) a silane or siloxane having amino groups in its molecule, in the presence of (iii) a crosslinking agent, and (iv) a surfactant, dispersed in (v) an aqueous polar phase.

2. A method of treating hair, skin or the Underarm according to claim 1 in which the organic quaternary ammonium compound having epoxide groups is glycidyl trimethylammonium chloride or glycidyl trimethylammonium bromide.

3. A method of treating hair, skin or the Underarm according to claim 1 in which the organic quaternary ammonium compound having halohydrin groups is selected from the group consisting of
(3-chloro-2-hydroxypropyl)trimethylammonium chloride,
(3-chloro-2-hydroxypropyl)dimethyldodecylammonium chloride,
(3-chloro-2-hydroxypropyl)dimethyloctadecylammonium chloride,
(3-chloro-2-hydroxypropyl)trimethylammonium bromide,
(3-chloro-2-hydroxypropyl)dimethyldodecylammonium bromide, and
(3-chloro-2-hydroxypropyl)dimethyloctadecylammonium bromide.

4. A method of treating hair, skin or the Underarm according to claim 1 in which the aqueous polar phase is water.

5. A method of treating hair, skin or the Underarm according to claim 1 in which the aqueous polar phase comprises water and a polar organic compound.

6. A method of treating hair, skin or the Underarm according to claim 5 in which the polar organic compound is selected from the group consisting of monohydroxy alcohols, diols, triols, glycerol esters, and polyglycols.

7. A method of treating hair, skin or the Underarm according to claim 1 in which the crosslinking agent is selected from the group consisting of organic epoxides containing at least two epoxy groups, epoxy functional silicones containing at least two epoxy groups, chlorohydrins, substituted di(meth)acrylates, unsubstituted di(meth)acrylates, oligo(meth)acrylates, substituted mono(meth)acrylates, hydroxyalkyl acrylates, and isocyanates.

8. A method of treating hair, skin or the Underarm according to claim 1 in which the hair, skin, or the underarm is treated with a cellulosic substrate, synthetic nonwoven substrate, wet-cleansing wipe, tissue, or towel, each of which contains the oil-in-water (O/W) or water-in-oil (W/O) emulsion or microemulsion composition.

9. An antiperspirant, deodorant, skin cream, skin care lotion, moisturizer, facial treatment, acne remover, wrinkle remover, personal cleanser, facial cleanser, bath oil, perfume, cologne, sachet, sunscreen, pre-shave lotion, after-shave lotion, shaving soap, shaving lather, hair shampoo, hair conditioner, hair colorant, hair relaxer, hair spray, mousse, styling gel, permanent, depilatorie, cuticle coat, make-up, color cosmetic, foundation, blush, lipstick, eyeliner, mascara, oil remover, color cosmetic remover, bath powder, body powder, pharmaceutical, biocide, or biologically active substance, containing the oil-in-water (O/W) or water-in-oil (W/O) emulsion or microemulsion composition prepared according to the method as defined in claim 1.

* * * * *